United States Patent [19]

Heyn et al.

[11] Patent Number: 5,201,757
[45] Date of Patent: Apr. 13, 1993

[54] MEDIAL REGION DEPLOYMENT OF RADIALLY SELF-EXPANDING STENTS

[75] Inventors: Lawrence R. Heyn, Maple Grove; Liann M. Johnson, Minneapolis; Matthew T. Yurek, Bloomington, all of Minn.; Peter A. Basile, Lawrenceville, N.J.; Robert L. Berger, New Hope, Pa.

[73] Assignee: Schneider (USA) Inc., Plymouth, Minn.

[21] Appl. No.: 863,231

[22] Filed: Apr. 3, 1992

[51] Int. Cl.$^5$ .............................................. A61M 29/00
[52] U.S. Cl. .................................. 606/198; 606/200; 623/1; 623/12
[58] Field of Search ............... 606/191, 194, 198, 200; 623/1, 12; 128/898; 604/104–108

[56] References Cited

U.S. PATENT DOCUMENTS

| | | |
|---|---|---|
| 3,868,956 | 3/1975 | Alfidi et al. . |
| 4,553,545 | 11/1985 | Maass et al. . |
| 4,649,922 | 3/1987 | Wiktor . |
| 4,655,771 | 4/1987 | Wallsten . |
| 4,681,110 | 7/1987 | Wiktor . |
| 4,699,611 | 10/1987 | Bowden . |
| 4,732,152 | 3/1988 | Wallsten et al. . |
| 4,733,665 | 3/1988 | Palmaz . |
| 4,830,003 | 5/1989 | Wolff et al. . |
| 4,846,794 | 7/1989 | Hertzer . |
| 4,950,227 | 8/1990 | Savin et al. . |
| 4,954,126 | 9/1990 | Wallstén ............................ 606/198 |
| 5,034,001 | 7/1991 | Garrison et al. . |
| 5,041,093 | 8/1991 | Chu ..................................... 606/198 |
| 5,071,407 | 12/1991 | Termin et al. ..................... 606/194 |
| 5,147,379 | 9/1992 | Sabbagnhian et al. ............ 606/200 |
| 5,160,341 | 11/1992 | Brenneman et al. ............... 606/198 |

FOREIGN PATENT DOCUMENTS

WO90/05554 11/1989 PCT Int'l Appl. .

Primary Examiner—C. Fred Rosenbaum
Assistant Examiner—William Lewis
Attorney, Agent, or Firm—Haugen and Nikolai

[57] ABSTRACT

An apparatus for deploying a radially self-expanding stent includes proximal and distal sleeves respectively containing proximal and distal end portions of the stent in a reduced radius delivery configuration. The sleeves can abut one another and thus contain the entire length of the stent, or may be used in combination with an outer catheter surrounding the sleeves and containing the medial region of the stent. In either event, once the stent and sleeves are positioned at the intended fixation site, the sleeves are moved axially with respect to one another to permit radial self-expansion of the stent only over its medial region, while the sleeves continue to contain the axially outward regions of the stent. Eventually, upon sufficient movement of the sleeves axially relative to one another, the stent becomes totally free of the sleeves, resulting in radial expansion over the entire stent length. The axial relative movement of the sleeves can be controlled by two or more catheters mounted movably with respect to one another, one catheter integral with each of the sleeves. Alternative arrangements for separating the sleeves include an externally threaded inner catheter, and a dilatation balloon or membrane expandable to force the sleeves apart from one another.

37 Claims, 7 Drawing Sheets

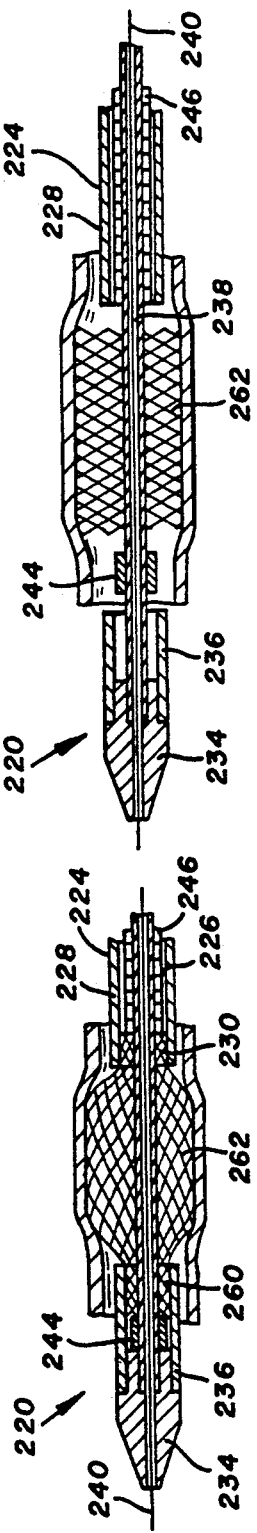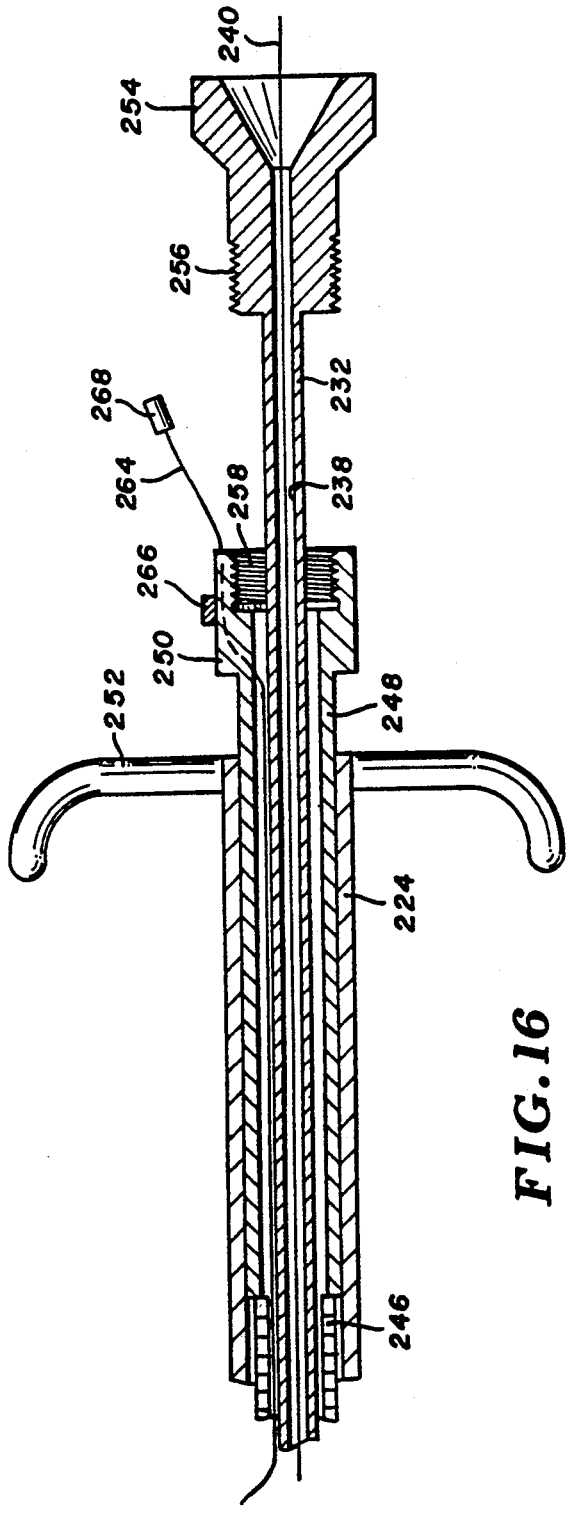
FIG.14
FIG.15
FIG.16

MEDIAL REGION DEPLOYMENT OF RADIALLY SELF-EXPANDING STENTS

BACKGROUND OF THE INVENTION

The present invention relates to body implantable prosthesis intended for long-term or permanent fixation in body cavities, and more particularly to the delivery and placement of self-expanding stents.

Self-expanding stents are employed in a variety of patient treatment and diagnostic procedures, for fixation in blood vessels, biliary ducts and other body lumens to maintain the passages. For example, a radially self-expanding stent can be deployed in an artery following a percutaneous transluminal coronary angioplasty (PCTA) or a percutaneous transluminal angioplasty (PTA) procedure. The stent resists any tendency in the vessel to close, thus countering acute reclosure and plaque restenosis.

A highly preferred construction for a radially self-expanding stent is disclosed in U.S. Pat. No. 4,655,771 (Wallsten), i.e. a flexible tubular braided structure formed of helically wound thread elements. Wallsten discloses a catheter for delivering the stent to the fixation site. Gripping members at opposite ends of the stent initially secure it to the catheter in an axially elongated, reduced radius configuration to enhance delivery. The proximal gripping member is movable distally, initially giving the stent covering the shape of a balloon. In complete deployment, the gripping members release the stent, allowing the stent to assume an axially shortened and radially expanded configuration, in contact with a blood vessel wall or other body tissue.

A similar stent construction is disclosed in U.S. Pat. No. 4,681,110 (Wiktor). A flexible tubular liner is constructed of braided strands of a flexible plastic, and is insertable into the aorta, whereupon it self-expands against an aneurism to direct blood flow past the aneurism. For delivery, the liner is radially compressed within the distal end of a main catheter tube. A secondary tube, inside the main catheter tubing and terminating just proximally of the liner, is held in place while the main tube is withdrawn, thus deploying the liner initially by its distal end.

A prevalent approach to deploying self-expanding stents, often referred to as the "rolling membrane" method, is shown in U.S. Pat. No. 4,732,152 (Wallsten et al). A hose or membrane is folded over upon itself to provide a double wall for maintaining a stent, radially compressed, at the distal end of a catheter or other delivery appliance. When the outer wall is moved proximally, a distal fold likewise travels proximally to expose the stent and allow radial expansion, beginning at the distal end of the stent. As compared to the previously mentioned proximal and distal gripping members, the rolling membrane approach is preferred due to lower cost and increased reliability. There are disadvantages, however, including a lack of one-to-one correspondence between membrane movement and stent exposure, which hinders accurate positioning of the stent. The amount of radial expansion and axial shortening is difficult to predict in view of the uncertainty in lumen size and tissue response to the stent, interfering with accurate stent positioning as stent deployment progresses from one end to the other. This approach requires at least two clinicians or other operators, and does not allow for any reversal in deployment.

Therefore, it is an object to the present invention to provide an apparatus for deploying a radially self-expanding stent, initially only along a medial region of the stent while the axially outward end regions of the stent remain confined in a reduced radius configuration.

Another object of the invention is to provide an apparatus which allows and facilitates deployment of a self-expanding stent by an individual clinician or other user.

A further object is to provide an apparatus and process for deploying radially self-expanding stents in a manner that reduces potential trauma to body tissue.

Yet another object is to provide a process for deploying self-expanding stents that involves interruption and partial reversal of deployment, to facilitate moving the stent axially within a body lumen for more accurate fixation.

SUMMARY OF THE INVENTION

To achieve these and other objects, there is provided an apparatus for deploying a radially self-expanding stent within a body lumen. The apparatus includes a confinement means for maintaining an elongate, radially self-expanding stent in a reduced radius delivery configuration wherein the stent is radially compressed along its entire axial length. The confinement means includes a proximal member radially confining a proximal region of the stent, and a distal member radially confining a distal region of the stent. These members are movable axially with respect to one another toward and away from a confinement position in which they cooperate to maintain the stent in the delivery configuration. A flexible, elongate delivery means is provided for delivering the stent, when in the delivery configuration and disposed near a distal end of the delivery means, to a deployment site in the body lumen. The delivery means includes a control means, operably associated with the confinement means, for moving the proximal and distal members axially relative to each other away from the confinement position to allow an initial radial self-expansion of the stent, only along a medial region thereof as the proximal and distal members continue to radially confine their respective end regions of the stent axially outwardly of the medial region. The control means further is operable to move the proximal and distal members axially away from the end regions following the initial expansion, to release the stent for radial self-expansion along its entire axial length.

Preferably the proximal and distal members comprise sleeves substantially equal to one another in their interior diameters, and abutting one another along an interface in a radially extended mid-plane of the stent. Alternatively the sleeves may cover less than the entire length of the stent, and cooperate with a further confining means, e.g. a catheter surrounding both sleeves and the medial region of the stent.

One preferred delivery means is a length of catheter tubing integral with the proximal sleeve and having a lumen. A second length of catheter tubing, contained within the lumen, provides the control means by virtue of its connection to a distal tip, which tip is also is connected to the distal sleeve. Accordingly, movement of the inner catheter relative to the outer catheter moves the distal sleeve relative to the proximal sleeve. The inside catheter can have a lumen to accommodate a guide wire used to initially position the catheters.

In an alternative embodiment, a key and slot arrangement fastens the proximal and distal sleeves together about an elongate dilatation balloon. A guide wire, surrounded by the balloon and sleeves, provides the delivery means. For deployment, the balloon is inflated by supplying a fluid under pressure to the balloon. Balloon expansion overcomes the force of the slots and keys to separate the sleeves, eventually to the point where the stent becomes totally free of the sleeves.

Further alternatives include an internal tube threadedly engaged with hubs secured to the proximal and distal sleeves. The threads associated with the respective sleeves follow opposite conventions, e.g. threads associated with the proximal sleeve being "righthand" and those associated with the distal sleeve being "lefthand". Rotating the internal tube thus moves the sleeves axially, either toward one another or away from one another. Finally, a flexible, substantially fluid tight membrane can join the proximal and distal sleeves through respective end walls integral with the sleeves. Fluid supplied to a cylinder formed by the membrane and sleeves inflates the cylinder to drive the sleeves axially apart from one another, eventually freeing the stent.

In yet another embodiment, a radial self-expanding stent is maintained in a reduced-radius delivery configuration, by virtue of its opposite end regions being retained by a frictional engagement. More particularly, the stent surrounds an inner catheter contained within the lumen of an outer catheter. A proximal end region of the stent is held by friction between the inner catheter and the distal end of the outer catheter. The distal end of the catheter is similarly held between the inner catheter and a distal sleeve integral with a distal tip of a deployment device. In this embodiment, medial region of the stent is exposed.

The stent is deployed by moving the inner catheter, and thus the distal tip, proximally relative to the outer catheter, which allows the medial region of the stent to radially self-expand while the proximal and distal en regions remain frictionally engaged. After this initial expansion, the distal end region can be released by locking a detent mounted slidably at the distal end of the inner catheter, then moving the inner catheter, distal tip and distal sleeve in the distal direction. The proximal end region can be released by moving the outer catheter in the proximal direction relative to the inner catheter, with a proximal detent preventing the stent from moving proximally with the outer catheter.

The apparatus is advantageously used in a process for deploying a radially self-expanding stent within a body lumen, including the following steps:

confining a radially self-expanding stent in a reduced radius delivery configuration, with a retaining means including proximal and distal members confining respective proximal and distal regions of the stent, while guiding the stent and the enclosure to a point at least proximate to a predetermined site within a body lumen and along a tissue wall segment defining the body lumen, the stent including a medial region between the distal and proximal regions;

with the enclosure near the predetermined site, moving first and second members axially relative to one another to permit an initial radial expansion of the stent only along the medial region while confining the proximal and distal regions of the stent against radial expansion with the first and second enclosure sections, respectively; and after the initial expansion, moving the proximal and distal members axially away from the proximal and distal regions to allow a self-expansion of the stent axially outwardly of the medial region along the proximal and distal regions, until the stent is free of the proximal and distal members and is radially expanded and in contact with the tissue wall segment along its entire axial length.

Substantial advantages arise from the fact that the stent is deployed medially, rather than from one of its ends to the other. First, positioning accuracy is enhanced, since the stent tends to remain centered at the intended fixation point. Radial expansion and axial shortening occur on both sides of the stent medial region, substantially symmetrically during release of the stent, minimizing the tendency of this behavior to draw the stent off center. The potential for trauma to a blood vessel wall or other tissue is reduced, in that the initially deployed medial region of the stent has no sharp ends or edges, such as might be present at the stent axial ends. Shortening of the stent does not occur with a fully expanded stent end in contact with the vessel wall. Rather, a fully expanded medial portion of the stent is between enclosures, i.e. the stent does not drag along the vessel wall as it shortens.

Further contributing to accuracy and fixation is the fact that in many cases the stent can be partially deployed, and in most instances at least partially reverse deployed, through axial movement of the members. Thus, a partially deployed stent with its outer end regions remaining radially confined, may be moved axially along a blood vessel or other lumen to more accurately place the stent. Alternatively, the proximal and distal members can be moved axially again to radially reduce portions of the stent earlier allowed to expand, which of course further facilitates axial movement of the stent in the enclosure.

The stent confining sleeves are not subject to the stresses at folds or creases inherent in the rolling membrane technique, and further can be used by a single operator with an improved "sense" for accurate stent positioning, given the one-to-one correspondence between relative sleeve movement and initial axial exposure of the stent.

IN THE DRAWINGS

Figure 6:
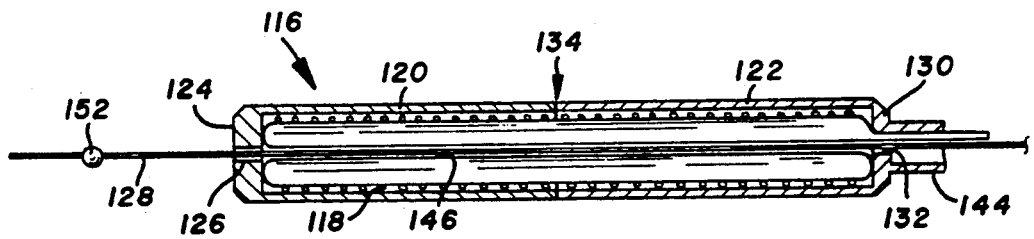
Figure 7:
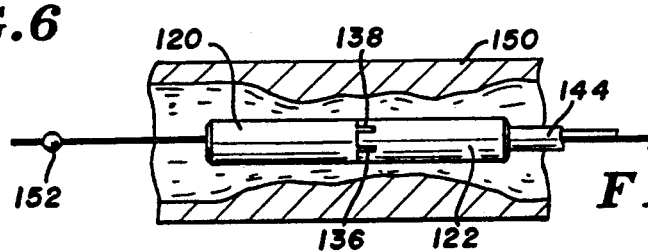
Figure 8:
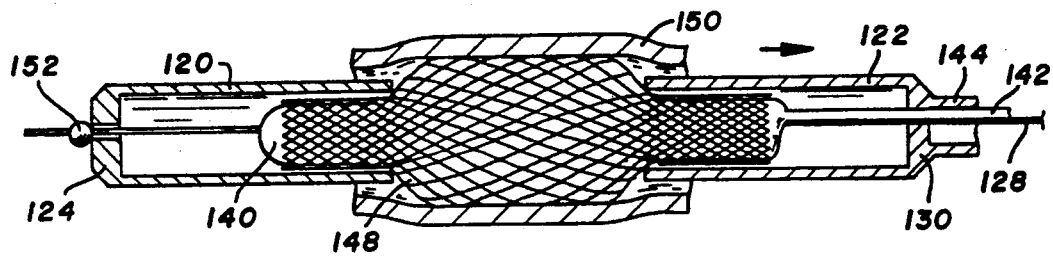
Figure 9:
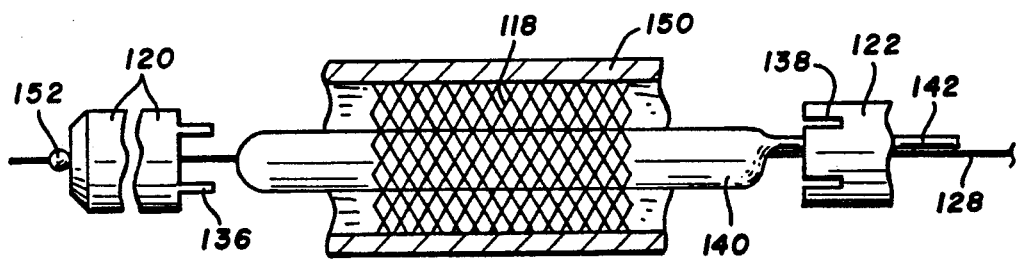
Figure 10:
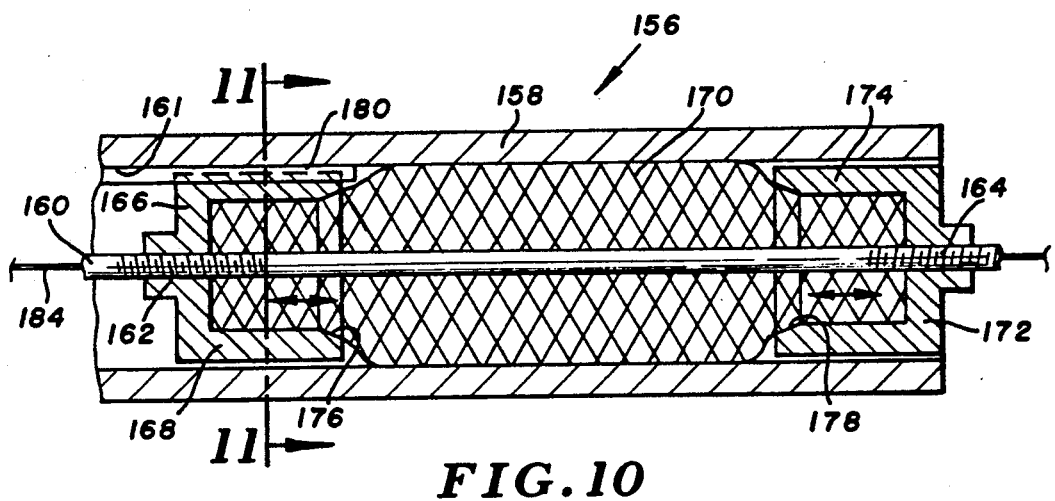
Figure 11:
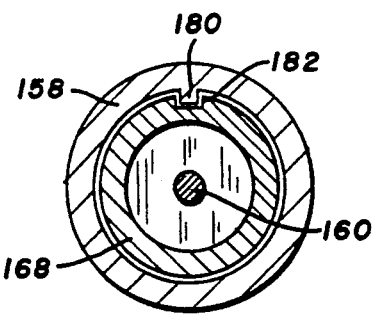
Figure 12:
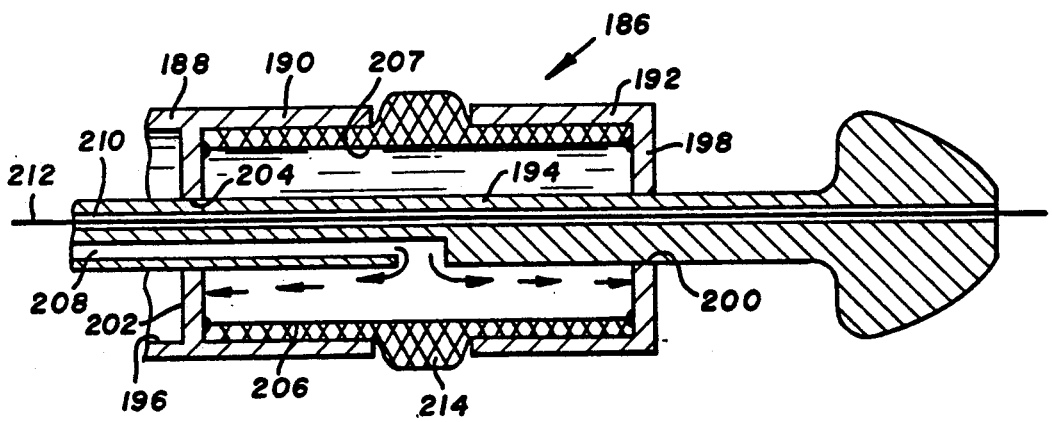
Figure 13:
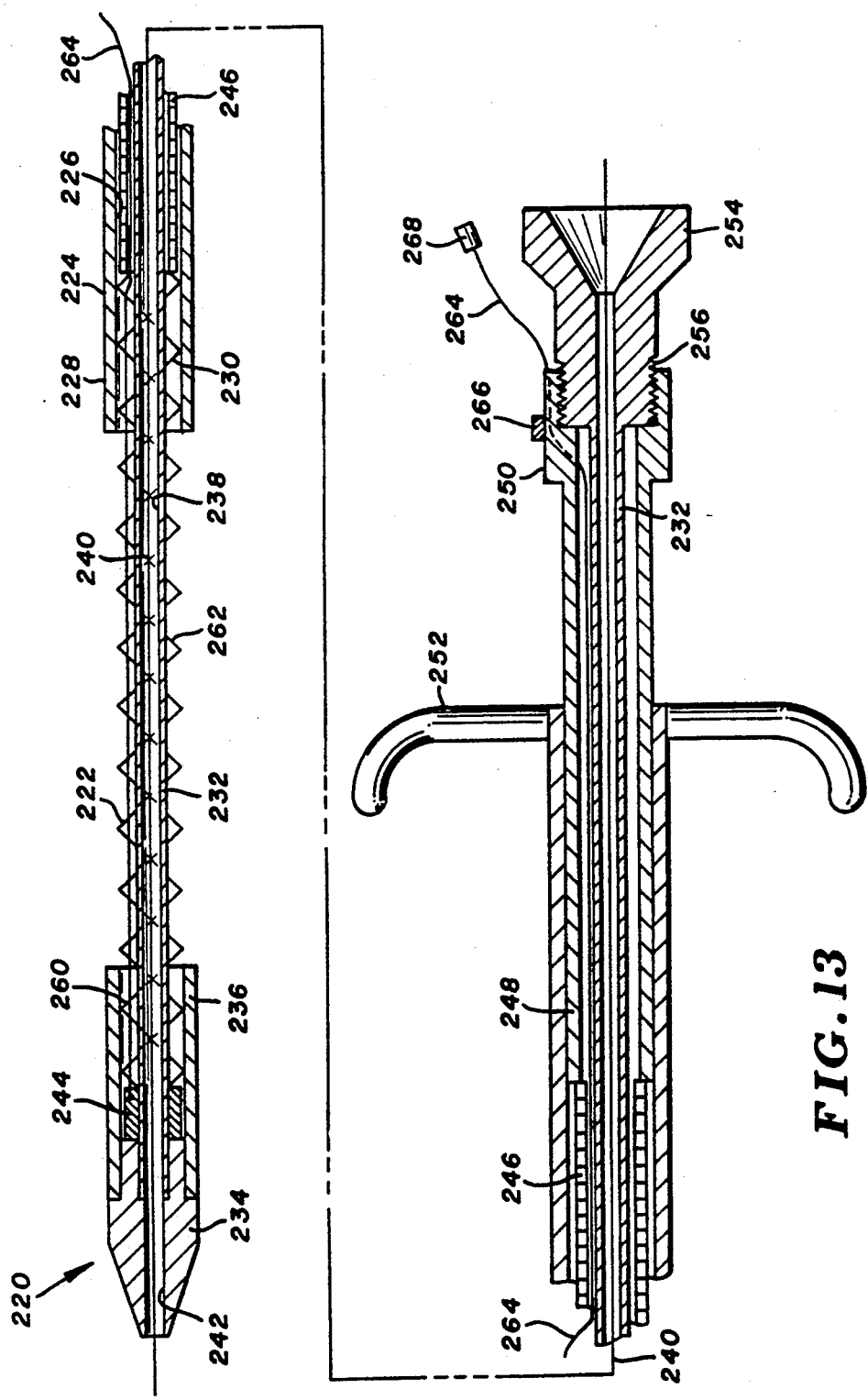

FIGS. 5a–d illustrate a sequence of stent deployment using the first embodiment device;

FIG. 6 is a side sectional view of a third embodiment stent deployment device;

FIGS. 7–9 illustrate a sequence of stent deployment using the third embodiment device;

FIG. 10 is a side sectional view of a fourth embodiment stent deployment device;

FIG. 11 is a sectional view taken along the line 11–11 in FIG. 10;

FIG. 12 is a side sectional view of a fifth embodiment stent deployment device;

FIG. 13 is a partial side sectional view of a sixth embodiment stent deployment device set to maintain the stent in a reduced radius configuration;

FIG. 14 illustrates the device of FIG. 13 with the stent at a stage of initial radial self-expansion; and FIG. 15 illustrates complete radial self-expansion of the stent; and FIG. 16 shows a proximal portion of the device, set to permit self-expansion of the stent.

DETAILED DESCRIPTION OF THE PREFERRED EMBODIMENTS

Figure 1:
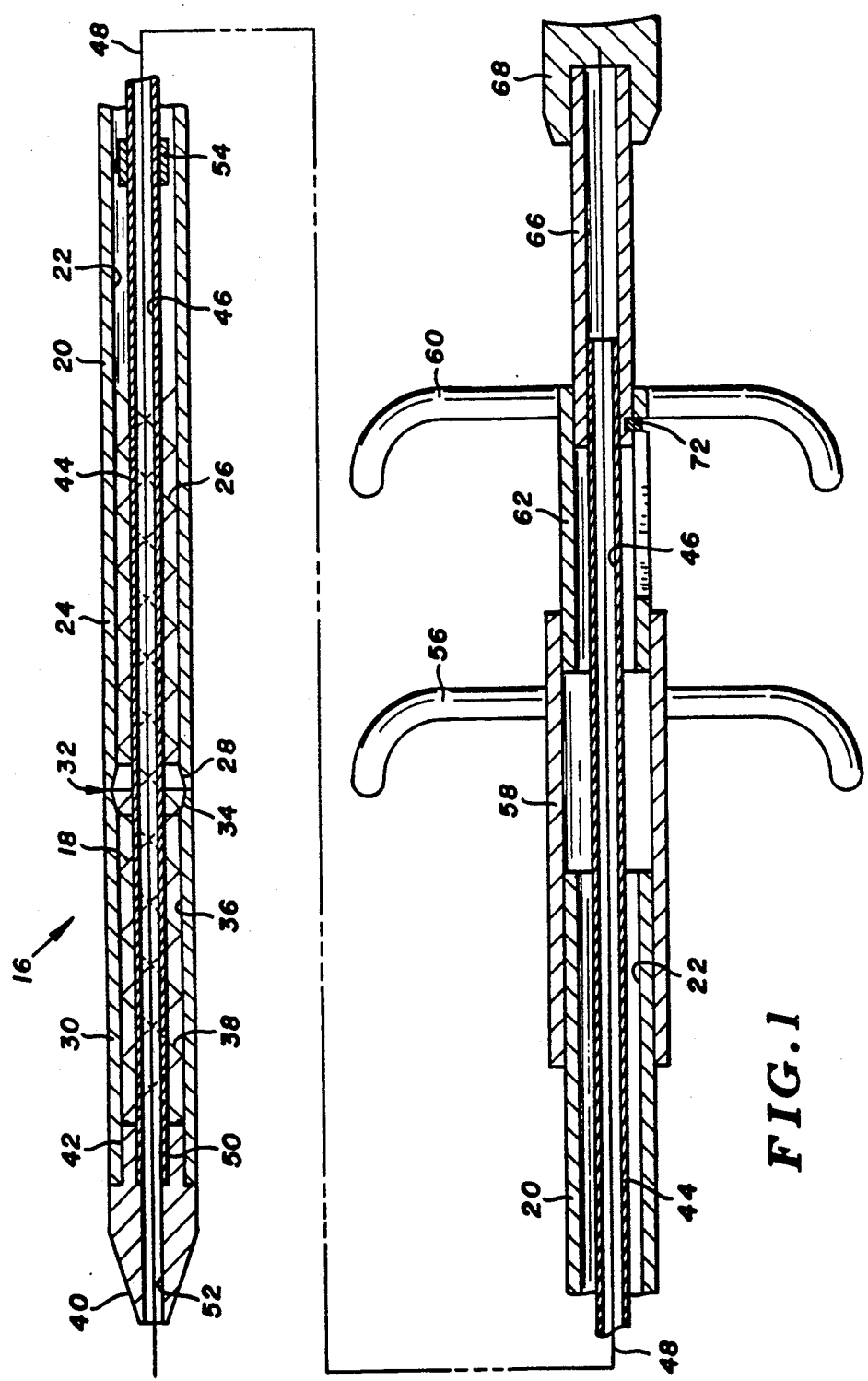
FIG. 1 is a partial side sectional view of a stent deployment device constructed according to the present invention.

Turning now to the drawings, there is shown in FIG. 1 a deployment device 16 for delivering a prothesis or stent 18 to an intended fixation location within a body lumen, and then controllably releasing the stent for radial self-expansion to a fixation within the lumen.

The device includes an elongate and flexible outer catheter 20 constructed of a biocompatible polymer, e.g. polyurethane, with an outside diameter of 0.12 inches or smaller. A central lumen 22 runs the length of catheter 20. A distal portion 24 of catheter 20 provides a sleeve that surrounds a proximal region 26 of stent 18. Sleeve 24 is inclined at its distal end to provide a frusto-conical inside surface 28 that facilitates release and re-capture of stent 18.

A distal sleeve 30 is contiguous with sleeve 24 at an annular interface 32. Sleeve 30 is formed at its proximal end with an inclined surface 34 similar to surface 28, and for the same purpose. A passage 36 through the distal sleeve forms a continuation of lumen 22, for a distal region 38 of the stent.

The distal end of sleeve 30 is fixed to a tapered distal tip 40, in an annular recess 42 formed in the tip. Also fixed to the distal tip is an inner catheter 44 with an outside diameter of approximately 0.08 inches or smaller and running substantially the length of device 16. Stent 18 surrounds inner catheter 44, and thus is confined between the inner and outer catheters. A lumen 46 in the inner catheter contains a flexible guide wire 48, and further is suitable for supplying fluids from the proximal end of the device for priming and addition of contrast media. The inner catheter is fixed into a cylindrical recess 50 formed in the distal tip, and the tip has a passage 52 continuing lumen 46.

Stent 18 has an open mesh or weave construction, formed of helically wound and braided strands or filaments of a resilient material, for example a body compatible metal (e.g. stainless steel) or polymer (e.g. polypropylene). As shown in FIG. 1, stent 18 is elastically deformed, into a reduced radius/increased axial length delivery configuration. Sleeves 24 and 30 cooperate to form an enclosure which confines the stent, maintaining it in the delivery configuration. When free of the sleeves, stent 18 radially self-expands, i.e. it elastically returns to a "normal" (free of external stress) configuration of increased radius and decreased axial length.

An annular detent 54, mounted to and surrounding inner catheter 44, occupies the space between the inner catheter and outer catheter 20 to limit proximal travel of stent 18 relative to the inner catheter. In this connection, it should be noted that the gap between the catheters appears much larger than the braided, helical strands forming stent 18. While suitable for illustrating various parts, it is to be understood that in actual practice, stent 18 occupies virtually all of the gap. Accordingly, it is desirable that the coefficient of friction between stent 18 and the inside surfaces of sleeves 24 and 30, be substantially less than the coefficient of friction between the stent and the outer surface of inner catheter 44. This difference in coefficients can be achieved by any combination of known means, including selection of different materials for the sleeves as opposed to the inner catheter, coating the interior surfaces of the sleeves with teflon or the like, and selectively abrading the exterior surface of the inner catheter.

Once stent 18, confined within sleeves 24 and 30, is delivered to its intended site of fixation, the sleeves are movable axially away from one another to release the stent. Of course, it is preferred that such severance to be accomplished by manipulating the device at a point remote from the fixation site, outside of the body. To this end, a stent release control structure is provided near the proximal end of device 16. In particular a finger grip 56 is mounted to a tubular section 58 which in turn is mounted to the proximal end of outer catheter 20. A finger grip 60 is mounted to a tubular section 62 in turn slidably mounted to tubular section 58. Finally, a proximal tubular section 66, supporting a proximal end member 68, is slidably mounted to tubular section 62 and fixed to the proximal end of inner catheter 44. A member 72 is mounted to proximal section 66 through tubular section 62, to fix sections 62 and 66 relative to one another. By moving finger grip 5 (and thus section 58) proximally or to the right as viewed in FIG. 1, outer catheter 20 and sleeve 24 are moved proximally away from distal sleeve 30, to deploy the proximal portion of stent 18. Distal movement of finger grip 60 moves distal sleeve 30 distally away from the more proximal sleeve 24, to deploy the distal portion of the stent. Either movement, or both in combination, will form a gap at interface 32 to allow limited radial expansion of stent 18, in particular near its center, while the proximal and distal regions remain confined between sleeves 24 and 30, respectively.

Figure 2:
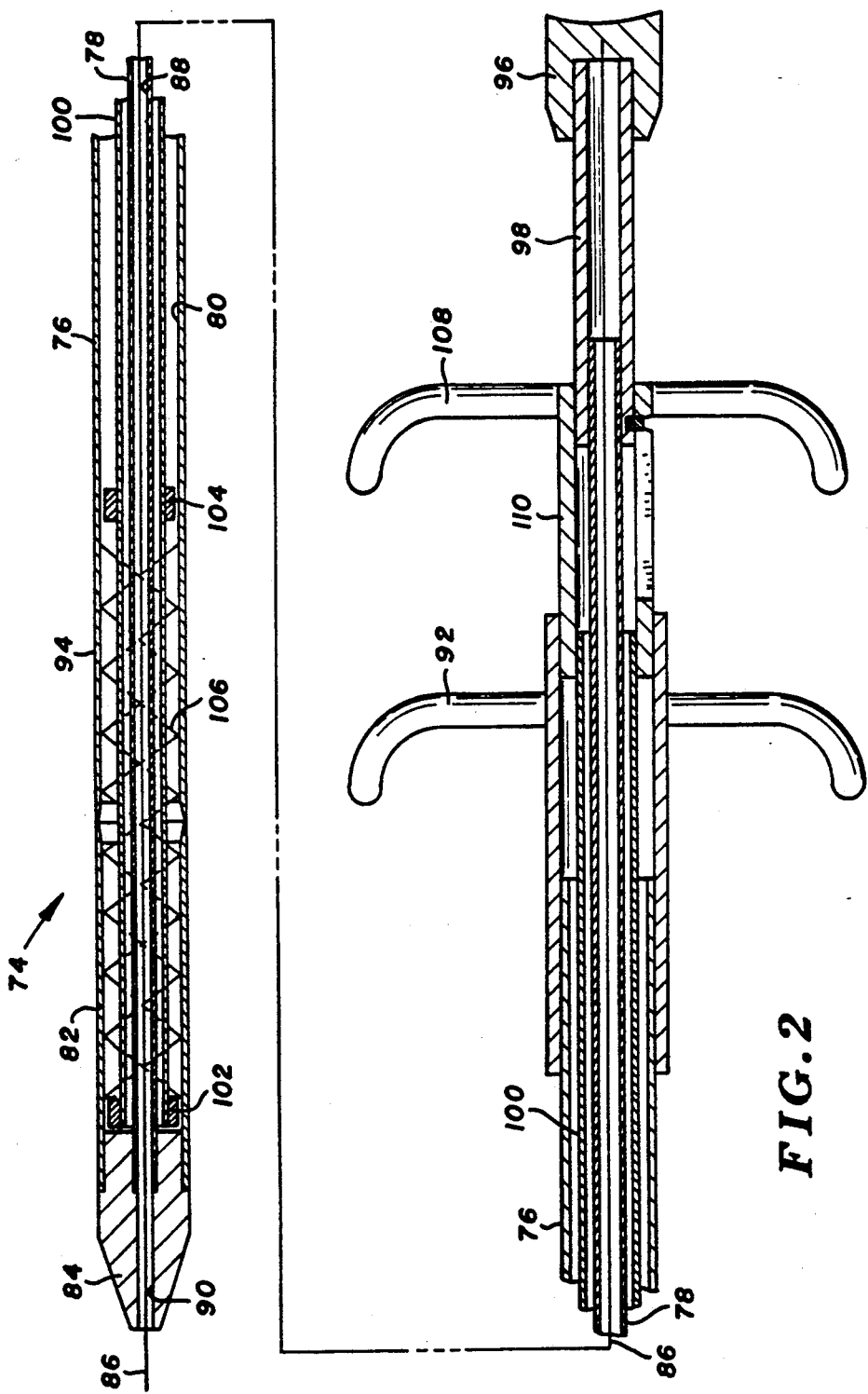
FIG. 2 is a view similar to that in FIG. 1, showing a second embodiment stent deployment device.

FIG. 2 shows a stent deployment device 74 similar to device 16 in that it includes an outer catheter 76 and an inner catheter 78 contained in a lumen 80 of the outer catheter. The inner catheter and a distal sleeve 82 are fixed to a tapered distal tip 84. A guide wire 86 is contained within a lumen 88 of the inner catheter and a passage 90 through the distal tip. Control means are provided near the proximal end of the device, including a finger grip 92 for moving a sleeve portion 94 of the outer catheter, and an end member 96 and tubular section 98 for axially moving inner catheter 78 and distal sleeve 82.

A departure from the construction of device 16 is that device 74 further incorporates an intermediate catheter 100 contained within lumen 80 and surrounding inner catheter 78. Annular detents 102 and 104, surrounding and secured to catheter 100 on opposite sides of a radially self-expanding stent 106, prevent any substantial axial travel of the stent relative to the intermediate catheter. Thus, by virtue of the connection of intermediate catheter 100 to a finger grip 108 and integral tubular section 110 the axial position of the intermediate catheter can be controlled from the proximal end of device 74, independently of the positions of sleeves 82 and 94.

Figure 3:
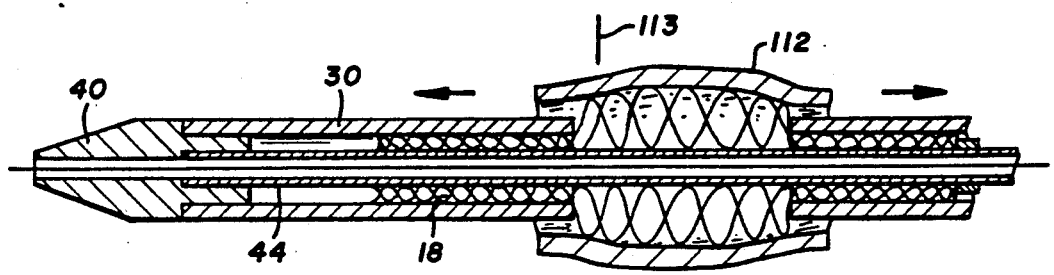
FIG. 3 is a side sectional view illustrating deployment of the stent using the first embodiment device.
Figure 4:
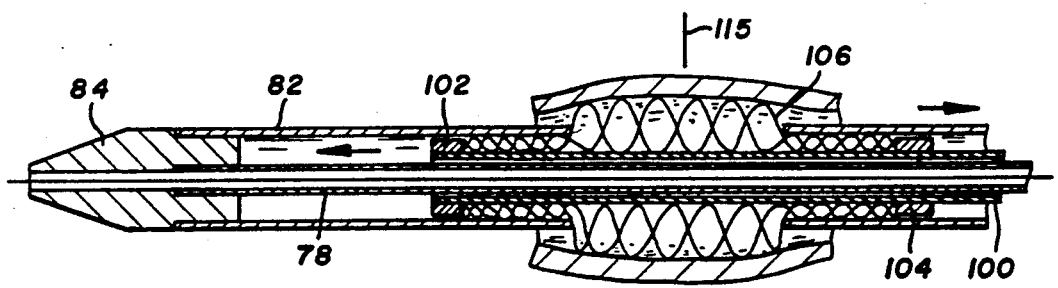
FIG. 4 is a side sectional view illustrating stent deployment using the second embodiment device.

Deployment of self-expanding stents, respectively by device 16 and by device 74, can be appreciated in comparing FIGS. 3 and 4. In FIG. 3, it is seen that initial radial expansion does not necessarily occur at the axial center or radially directed mid-plane of stent 18 (line 113), although it does occur along a medial region between the two axially outward end regions.

By contrast, it is seen from FIG. 4 that intermediate catheter 100 can be moved axially with respect to distal sleeve 82 and sleeve 94 of the outer catheter, for a preferred alignment of stent 106 with the gap between the sleeves, whereby initial radial expansion occurs at and remains symmetrical about the mid-plane 115 of the stent.

Another alternative to device 74 provides a similar symmetrical deployment if desired. In particular, such alternative device (not shown) involves a catheter with a single annular detent at its distal end, used in lieu of catheter 100 and detents 102 and 104 in FIG. 2. The alternative catheter is positioned with its distal end proximal relative to the stent, i.e. where detent 104 appears in FIG. 2. As a further alternative, this catheter can be formed with sufficient wall thickness, at least along its distal end region, so that the distal region itself functions as a detent, in which case no separate detent is mounted to the catheter.

Figure 5A:
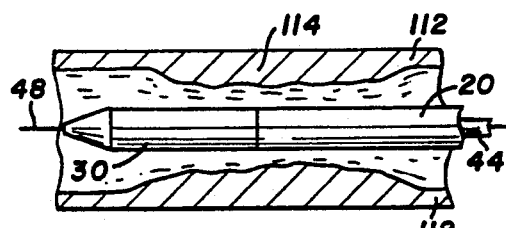

FIGS. 5a–d illustrate a sequence of deploying stent 18 using device 16, although deployment with device 74 is similar. FIG. 5a illustrates initial positioning of the stent, still contained within sleeves 24 and 30, within a blood vessel and along a generally annular tissue wall segment 112 forming the blood vessel. It can be assumed that tissue wall segment 112 has just been subject to a percutaneous transluminal angioplasty procedure, in which a dilatation balloon (not illustrated) has compressed plaque 114 or other unwanted tissue which, before the dilatation procedure, was constricting flow within the blood vessel. The purpose for fixating the self-expanding stent is to prevent acute closure of the vessel and inhibit restenosis.

Deployment of stent 18 begins with a percutaneous insertion and transvenous movement of guide wire 48 to a point just beyond, or distally of, tissue wall segment 112. The remainder of device 16, including the radially constrained stent, is inserted over guide wire 48 and thus is guided toward the desired treatment location, until sleeves 24 and 30 are positioned at least proximate the desired treatment location, as illustrated in FIG. 5a.

Figure 5B:
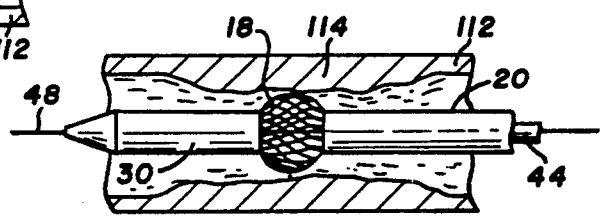

In FIG. 5b, separation and partial removal of the sleeves from one another has permitted an initial radial expansion of stent 18 along its medial region. At this point the position of stent 18 can be observed using radiopaque markers on the distal tip and detent 54. If the axial stent position is not as intended, the stent and sleeves at this stage are easily moved in either axial direction. Further, should reversal of the deployment be desired, due to a need to adjust positioning or for any other reason, sleeves 24 and 30 can be moved towards one another to recapture the stent. Tapered surfaces 28 and 34 facilitate recapture, just as they facilitate initial release and expansion of the stent when the sleeves are first moved apart from one another.

Generally, deployment is reversible if stent 18 is open to one fourth or less of its full expansion, although factors such as the stent and sleeve materials, angle of the helical braided strands in the stent, and expanded stent size as compared to sleeve diameter, all influence the ability to recapture the stent at any given stage of deployment.

Figure 5C:
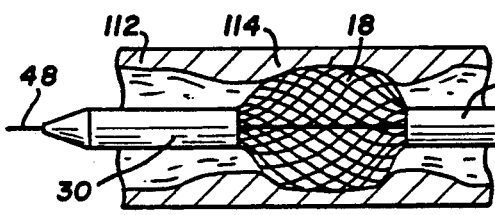

At the stage illustrated in FIG. 5c, release of the stent has progressed beyond the point of recapture. Nonetheless, axial travel to adjust the stent position remains practicable, and as compared to the rolling membrane deployment approach, is bi-directional and less likely to cause trauma to tissue wall segment 112, because the proximal and distal ends of the stent remain confined within sleeves 24 and 30, respectively.

Figure 5D:
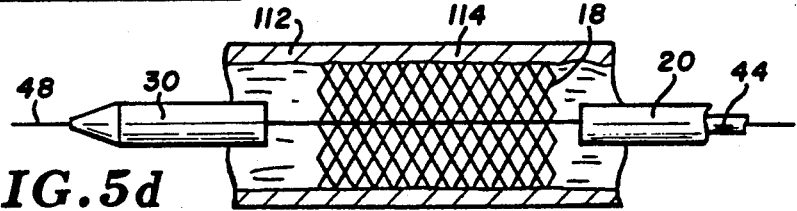

Complete deployment is seen in FIG. 5d, where stent 18 is completely free of the sleeves, radially expanded over its entire axial length, and thus in contact with tissue wall segment 112 over its full length. The radius of the expanded stent is substantially greater than the radius of outer catheter 20, facilitating the removal of device 16 by withdrawal of the distal end of the device through the expanded stent. Grips 56 and 60 are used to bring sleeves 24 and 30 together before withdrawal, if desired.

FIGS. 6–9 illustrate another alternative deployment device 116 in which a self-expanding stent 118 is radially compressed and contained between a distal sleeve 120 and a proximal sleeve 122. A distal end cap or wall 124 is integral with the distal sleeve and has a distal opening 126 to permit passage of a guide wire 128. At the opposite end of the enclosure formed by the sleeves is a proximal end wall 130 having an opening 132 to admit the guide wire. Sleeves 120 and 122 are releasably connected to one another at an interface 134 by a plurality of interlocking keys 136 and slots 138.

A dilatation balloon 140 is contained within the enclosure formed by the sleeves, and surrounded by stent 118. The balloon is flexible and can be expanded by introducing a fluid under pressure through a balloon inflation catheter 142 passing through opening 132 with the guide wire, with the inflation catheter and the guide wire both contained in an outer catheter 144. It is to be appreciated that this arrangement could be replaced by a single catheter with a balloon inflation lumen and second lumen to accommodate the guide wire. Balloon 140 preferably is toroidal, having an axial passage 146 for admitting the guide wire.

As seen from FIG. 7, sleeves 120 and 122 and constrained stent 118 are aligned for fixation in much the same manner as in the earlier described embodiments. Once again, radial self-expansion occurs first along a medial region 148 of the stent, responsive to the axial separation of sleeves 120 and 122 from one another. Separation is accomplished through a flexible expansion of balloon 140. Initially, inflation provides an axial force, acting in opposite directions against proximal and distal end walls 130 and 124, to overcome the retaining force of the keys and slots. Once the sleeves are separated, portions of the dilatation balloon expand radially outwardly and enter the gap between the sleeves (FIG. 8), to provide a further force tending to move the sleeves axially away from one another. As before, radial expansion of the stent occurs in the gap.

As seen in FIG. 9, continued inflation of balloon 140 eventually moves sleeves 120 and 122 sufficiently far apart from one another to completely free stent 118 for radial expansion over its entire length, shown in contact with a tissue wall segment 150. The fully expanded stent is large enough in diameter to facilitate withdrawal of device 116 proximally through the stent. A stop 152 fixed to guide wire 128 to the left of distal wall 124 as viewed in FIG. 6, is larger in diameter than opening 126, such that withdrawing the guide wire also withdraws distal sleeve 120 and the remainder of device 116.

FIG. 10 shows a further alternative deployment apparatus 156 including an outer catheter 158 and an inner catheter 160 contained within a lumen 161 of the outer catheter. The inner catheter is provided with external threads along two sections of its length, as indicated at 162 and 164. Section 162 is threadedly engaged with internal threads of an opening through a proximal wall or hub 166 integral with a proximal sleeve 168, which contains a proximal end region of a stent 170 in a reduced radius delivery configuration. Section 164 of the inner catheter is threadedly engaged with the internal threads of a distal hub 172 integral with a distal sleeve 174, which contains a distal end region of the stent. Tapered inside surfaces of the sleeves, at 176 and 178, respectively, facilitate stent self-expansion.

The threads at sections 162 and 164 follow opposite conventions, one of the sections being "lefthand" while the other is "righthand". Accordingly, rotation of catheter 160 in one direction moves sleeves 168 and 174 towards one another, while catheter rotation in the opposite direction moves the sleeves longitudinally away from one another. Catheter 160 can be rotated using means (not shown) at the proximal end of the device. FIG. 11 illustrates a key 180 integral with outer catheter 158 and a slot 182 in sleeve 168 that accommodates the key, thus to prevent the proximal sleeve from rotating with the inner catheter. A similar arrangement can be provided to maintain distal sleeve 174 if desired, although it is to be appreciated that axial movement of just one of the sleeves in response to inner catheter rotation is sufficient for deployment.

When used to deploy stent 170, device 156 is guided to the intended fixation site over guide wire 184. Outer catheter 158 is withdrawn proximally to expose the medial region of stent 170 between sleeves 168 and 174, thus to permit immediate radial self-expansion of the medial region. Following any desired axial repositioning of the stent and sleeves, inner catheter 160 is rotated in the direction to move the sleeves apart from one another, until the axially outward regions of the stent are free of the sleeves. The diameter of the radially expanded stent is sufficient to permit withdrawal of the sleeves proximally through the stent.

To provide for reverse deployment, the axial length of sleeves 168 and 174 can be increased as compared to that shown in FIG. 10, to the point where the sleeves abut one another, in which case the sleeves would contain the stent, without the need for outer catheter 158.

Yet another stent deployment device 186 is illustrated in FIG. 12, including an outer catheter 188 integral with a proximal sleeve 190, a distal sleeve 192 and an inner catheter 194 within a lumen 196 of the outer catheter. Proximal sleeve 190 has a proximal wall 202 with an opening 204, and distal sleeve 192 has a distal wall 198 with an opening 200. Openings 200 and 204 admit the inner catheter and permit sliding, but have a tight, sealing relation to the inner catheter. An expandable membrane 206, connected between end walls 198 and 202, forms with the walls a substantially fluid tight chamber 207. A fluid lumen 208 in inner catheter 194 is open to the chamber, for supplying fluid under pressure to the chamber. Catheter 194 includes another lumen 210 to accommodate a guide wire 212. A stent 214 surrounds membrane 206 and is contained in the delivery configuration by sleeves 190 and 192. Membrane 206 preferably is connected to the end walls, but need not be, so long as it can be expanded by supply of fluid to chamber 207 through lumen 208 that exceeds the rate of fluid flow out of the chamber.

Stent 214 is deployed by supplying fluid under pressure to chamber 207, which expands the membrane to urge sleeves 190 and 192 axially apart from one another. Upon separation of the sleeves, the membrane tends to bulge radially outward into the gap between the sleeves, further tending to separate the sleeves, permitting radial self-expansion of stent 214 along its medial region.

FIGS. 13–16 illustrate another alternative deployment device 220 for delivering a stent 222 to an intended fixation location, followed by a controlled release of the stent for radial self-expansion and fixation. The device includes an elongate and flexible outer catheter 224 constructed of a biocompatible polymer, and having a central lumen 226 running the length of the catheter 224. A distal portion 228 of the catheter provides a sleeve that surrounds a proximal region 230 of the stent.

An inner catheter 232, contained within lumen 226, runs substantially the length of the device, including a substantial distal portion extending beyond the distal end of outer catheter 224. A tapered distal tip 234 is fixed to the distal end of inner catheter 232. A distal sleeve 236, also fixed to the distal tip, surrounds the inner catheter. A lumen 238 through inner catheter 232 contains a guidewire 240, and also is suitable for supplying fluids from a proximal end of the device, for priming and an addition of contrast media. The inner catheter is fixed to a cylindrical recess formed in the distal tip, and the tip has a passage continuing lumen 238.

An annular distal detent 244 surrounds inner catheter 232 near tip 234, and is mounted slidably on the inner catheter. Just proximally of stent 222, a coil 246 surrounds the inner catheter and extends in the proximal direction to a length of tubing 248 integral with a handle 250. A T-shaped handle 252 is integral with outer catheter 224. Inner catheter 232 extends proximally to a hub 254. Hub 254 includes external threads 256 which, when engaged with internal threads 258 of handle 250, lock the axial position of the hub relative to handle 250. When the hub and handle are threadedly engaged as shown in FIG. 13, inner catheter 232 is at its most distal position with respect to outer catheter 224. Stent 222 surrounds the inner catheter and is held at both ends by friction. More particularly, a distal region 260 of the stent is frictionally engaged between distal sleeve 236 and inner catheter 232, while proximal region 230 of the stent is frictionally engaged between distal portion 228 and the inner catheter. Accordingly, a medial region 262 of the stent remains in a reduced-radius delivery configuration, despite being exposed along the distance between the proximal and distal sleeves. So long as hub 254 remains threadedly engaged within handle 250, stent 222 is retained in the delivery configuration.

Once stent 222 is positioned as desired along a body lumen, it is allowed to radially self-expand, initially only along medial region 262 as seen in FIG. 14. This initial expansion is accomplished by disengaging hub 254 from handle 250, whereupon the residual elastic force in the stent causes the stent to radially expand along the medial region, and simultaneously draws distal tip 234, sleeve 236 and inner catheter 232 in the proximal direction relative to handle 250. To enhance the effect of the residual elastic stent force, the operator can pull hub 254 in the proximal direction away from handle 250. In any event, the handle and hub become spaced apart as illustrated in FIG. 16, and medial region 262 of the stent is axially contracted and radially expanded, with the medial region contacting a vessel wall as shown in FIG. 14.

At this point, a proper positioning of the stent can be verified. If the stent requires repositioning, the operator need only move hub 254 distally toward handle 250, to at least partially radially contract stent 222. In the reduced radius configuration, the stent can be readily repositioned as desired.

With the stent properly positioned, deployment is completed by releasing the proximal and distal regions. As a result, stent 222 contacts the vessel wall along its entire length, as seen in FIG. 15. The distal end region is released by moving hub 254 in the distal direction toward handle 250. (This is the same motion that radially contracts stent 222, as long as distal end region 260 remains captured within distal sleeve 236).

To release the distal end region, distal detent 244 is "locked" with respect to handle 250, by releasibly locking a wire 264 within a slit in handle 250, with a wire lock 266. Wire 264 is fixed at its distal end to the distal detent. A knob or grip 268 on wire 264, proximally of handle 250, facilitates manipulation of the wire. Thus, when movement of hub 254 toward the handle moves inner catheter 232 in the distal direction, detent 244 does not move with the inner catheter, and prevents the stent distal end region from moving with the inner catheter as well, until the distal end region is free of distal sleeve 236.

Proximal end region 230 of the stent is released by moving handle 250 in the distal direction toward handle 252, which causes outer catheter 224 to move proximally along and relative to inner catheter 232. Coil 246 functions as a proximal stop, to prevent the proximal end region of stent 222 from traveling in the proximal direction with the outer catheter. To this end, coil 246 can be stiffened with a wire (not shown) attached to the distal end of the coil and to handle 250, if desired. Consequently, by the time the distal end of outer catheter 224 is aligned with the distal end of coil 246, the proximal end region 230 is free to radially self-expand. The user can control the deployment of stent 222 by selectively releasing either one of distal end region 260 or proximal end region 230 before releasing the other.

Thus, in accordance with the present invention a variety of stent deployment devices may be employed to deliver a radially self-expanding stent, maintained in a reduced radius configuration, to the approximate site of delivery. Proximal and distal sleeves form releasably sections of a stent retainer, and permit the stent to radially self-expand along its medial region as the sleeves are moved axially with respect to one another. If desired, deployment can be interrupted at an early stage, and radiopaque markers other indicia checked to ensure accurate positioning. Trauma to surrounding tissue is minimized, as tissue is not exposed to the ends of stent until virtually the entire axial length of stent is self-expanded and essentially fixed relative to the tissue. The use of concentric, slidable catheters or a threaded internal catheter as the control means for axially moving the sleeves, provides the added advantage of stent recapture in the early stages of stent deployment.

What is claimed is:

1. An apparatus for deploying a radially self-expanding stent within a body lumen, including:

a retaining means for maintaining an elongate, radially self-expanding stent in a delivery configuration wherein the stent has a reduced radius along its entire axial length, the retaining means including a proximal member radially confining a proximal end region of the stent and a distal member radially confining a distal end region of the stent, the proximal and distal members being movable axially with respect to one another toward and away from a confinement position in which the members, while so confining their respective end regions of the stent, cooperate to maintain the stent in the delivery configuration; and a flexible, elongate delivery means for delivering the stent, when in the delivery configuration and disposed near a distal end of the delivery means, to a deployment site in the body lumen, the delivery means including a control means operably associated with the confinement means for moving the proximal and distal members axially with respect to each other away from the confinement position to allow an initial radial self-expansion of the stent only along a medial region between the end regions as the proximal and distal members continue to radially confine said respective end regions, and further for moving the proximal and distal members axially relative to said respective end regions following the initial self-expansion, to release the stent for radial self-expansion along its entire axial length.

2. The apparatus of claim 1 wherein:

said control means, when moving the proximal and distal members away from the confinement position, moves said members axially away from one another to allow the initial radial self-expansion, and releases the stent by moving the proximal and distal members further axially away from one another following the initial radial self-expansion.

3. The apparatus of claim 2 wherein:

said proximal and distal members respectively comprise proximal and distal sleeves respectively radially confining the proximal and distal regions of the stent.

4. The apparatus of claim 3 wherein:

said proximal and distal sleeves are substantially equal to one another in interior diameter and, when so confining the stent, surround the stent and abut one another along an interface.

5. The apparatus of claim 4 wherein:

said interface is in the radially extended mid-plane of the stent.

6. The apparatus of claim 4 wherein:

said delivery means include a first length of catheter tubing integral with the proximal sleeve and having a first lumen, and wherein the control means includes an elongate moving member running substantially the length of the first catheter tubing and contained within the first lumen, a means securing the moving member integrally with the distal sleeve, and a means for moving the moving member distally with respect to the first catheter tubing.

7. The apparatus of claim 6 wherein:

said moving member comprises a second length of catheter tubing surrounded by the stent and having a second lumen, and the means for securing the moving member include a distal tip fixed to the respective distal ends of the distal sleeve and the second length of catheter tubing.

8. The apparatus of claim 7 wherein:

said delivery means further includes a flexible guide wire contained within the second lumen.

9. The apparatus of claim 8 further including:

a detent means mounted to the second catheter tubing proximally of the stent, to limit proximal movement of the stent with respect to the second- catheter tubing.

10. The apparatus of claim 9 wherein:

said proximal sleeve comprises a distal end portion of the first catheter tubing.

11. The apparatus of claim 8 wherein:
said control means further includes a third length of catheter tubing within the first lumen, surrounding the second catheter tubing, and moveable axially relative to the first catheter tubing and the second catheter tubing.

12. The apparatus of claim 11 wherein:
said stent surrounds the third catheter tubing, and wherein first and second detents are mounted to the third catheter tubing and disposed on opposite sides of the stent, to limit axial travel of the stent with respect to the third catheter tubing.

13. The apparatus of claim 12 wherein:
said proximal sleeve comprises a distal end portion of the first catheter tubing.

14. The apparatus of claim 4 wherein:
said delivery means includes an elongate and flexible guide wire and an elongate dilatation balloon at the distal end of the guide wire, a fastening means for releasably securing the proximal and distal sleeves to one another at the interface with the sleeves surrounding the balloon, and a balloon inflation means for supplying a fluid under pressure to the balloon to effect an elastic expansion of the balloon, the expansion overcoming the retaining force of the fastening means to move the proximal and distal sleeves axially away from one another.

15. The apparatus of claim 14 wherein:
said balloon is annular and surrounds the guide wire.

16. The apparatus of claim 15 further including:
proximal and distal end walls integral with the proximal and distal sleeves, respectively, for further confining the balloon between the sleeves and including respective proximal and distal openings to accommodate the guide wire.

17. The apparatus of claim 16 further including:
a stop mounted integrally on the guide wire distally of the distal end wall and larger than the distal opening.

18. The apparatus of claim 15 wherein:
said balloon inflation means includes a length of catheter tubing having a lumen open to the interior of the balloon, for providing the fluid to the balloon.

19. The apparatus of claim 3 further including:
proximal and distal end walls integral with the proximal and distal sleeves, respectively, and including respective proximal and distal openings;
wherein the control means includes an elongate rotatable member having a first externally threaded section threadedly engaged within one of said proximal and distal openings corresponding to a selected one of the sleeves, and a means for rotating the rotatable member relative to the selected sleeve, thereby axially moving the selected sleeve alternatively toward and away from the other sleeve.

20. The apparatus of claim 19 wherein:
said rotatable member further includes a second threaded section threadedly engaged with the other sleeve, with respective first and second threads following opposite conventions.

21. The apparatus of claim 19 wherein:
said proximal and distal sleeves together surround less than the entire axial length of the stent, and wherein the delivery means includes a length of catheter tubing having a lumen, with a distal portion of the catheter tubing surrounding the proximal and distal sleeves to cooperate with the sleeves in radially confining the stent; and
wherein the rotatable member is contained within the lumen and runs substantially the length of the catheter tubing, the means for rotating the rotatable member being located at a proximal end of the catheter tubing.

22. The apparatus of claim 21, further including:
a means for preventing rotation of the selected sleeve with respect to the catheter tubing while the rotatable member is rotated.

23. The apparatus of claim 3 further including:
proximal and distal end walls integral with the proximal and distal sleeves, respectively;
wherein the control means include an expandable means cooperating with said proximal and distal end walls to form a fluid chamber surrounded by the stent; and a fluid supply means for supplying a fluid under pressure to the chamber, thereby to expand the expandable means and urge the proximal sleeve and distal sleeve away from one another.

24. The apparatus of claim 23 wherein:
said expandable means is connected to the proximal and distal end walls, whereby said fluid chamber is substantially fluid tight.

25. The apparatus of claim 24 wherein:
said proximal end wall and distal end wall include respective proximal and distal openings; and
wherein the fluid supply means includes a catheter contained in the proximal and distal openings in sliding and substantially sealed relation to the proximal and distal end walls, and a fluid lumen in the catheter open to the chamber.

26. The apparatus of claim 1 wherein:
said control means moves the proximal and distal members axially towards one another to allow the initial radial self-expansion.

27. The apparatus of claim 26 wherein:
said control means includes a proximal detent means for restraining the proximal end region to facilitate movement of the proximal member in the proximal direction relative to the proximal end region, and a distal detent means for restraining the distal end region to facilitate distal movement of the distal member relative to the distal end region.

28. The apparatus of claim 27 wherein:
said proximal and distal members respectively comprise proximal and distal sleeves respectively radially confining the proximal and distal end regions of the stent.

29. The apparatus of claim 28 wherein:
said delivery means includes a handle means, a first elongate moving member integral with the proximal sleeve and mounted at its proximal end for axial movement relative to the handle means, and a second elongate moving member running substantially the length of the first elongate moving member, said second moving member being integral with the distal sleeve and mounted at its proximal portion for axial movement relative to the handle means, and wherein the control means includes means for moving the first and second moving members axially with respect to the handle means.

30. The apparatus of claim 29 wherein:
said first moving member comprises a first length of catheter tubing having a first lumen, and wherein said second moving member comprises a second length of catheter tubing contained within th first lumen, and wherein the proximal end region of the stent is maintained between the second length of the catheter tubing and the proximal sleeve by frictional engagement, and the distal end region of the stent is maintained between the second length of catheter tubing and the distal sleeve by frictional engagement.

31. The apparatus of claim 30 wherein:
said proximal sleeve comprises a distal end portion of the first catheter tubing.

32. The apparatus of claim 30 wherein:
said distal detent means is integrally mounted to the second length of catheter tubing distally of the stent, and the proximal detent means is mounted with respect to the handle means and disposed proximally of the stent.

33. The apparatus of claim 32 wherein:
said distal detent means is mounted slidably on the second length of catheter tubing, and wherein the control means further includes means for maintaining the distal detent means substantially axially fixed relative to the handle means as the second length of catheter tubing is moved distally relative to the handle means.

34. A process for deploying a radially self-expanding stent within a body lumen, including the steps of:
confining a radially self-expanding stent in a reduced radius delivery configuration with a retaining device including proximal and distal members confining respective proximal and distal regions of the stent, while guiding the stent to a point at least proximate a predetermined site within a body lumen and along a tissue wall segment defining the body lumen, the stent including a distal end region, a proximal end region and a medial region between the distal and proximal regions;
with the enclosure at the predetermined site, moving first and second sections of the enclosure axially with respect to one another to permit an initial radial expansion of the stent only along the medial region while confining the proximal and distal regions of the stent against radial expansion with the first and second enclosure sections, respectively; and
after the initial expansion, further moving the first and second enclosure sections axially with respect to one another to allow a self-expansion of the stent progressing axially outwardly of the medial region along the proximal and distal regions, until the stent is free of the first and second enclosure sections and is radially expanded and in contact with the tissue wall segment along its entire axial length.

35. The process of claim 34 including the further step of:
after said initial expansion and prior to said further moving of the enclosure sections, determining whether the stent is positioned at the predetermined site and, responsive to determining the stent is not so positioned, moving the stent and the enclosure sections axially along the tissue wall segment toward the predetermined site.

36. The process of claim 35 including the further step of:
after said step of determining and prior to said step of moving the stent and the enclosure sections axially along the tissue wall segment, moving the first and second enclosure sections axially with respect to one another to at least partially radially contract the medial region of the stent.

37. The process of claim 34 wherein:
at least a portion of the medial region contacts the tissue wall segment after the initial expansion and before said further moving of the enclosure sections.

* * * * *